United States Patent
Michalske

(10) Patent No.: US 10,060,894 B2
(45) Date of Patent: Aug. 28, 2018

(54) METHOD AND DEVICE FOR DYNAMIC MONITORING OF GAS SENSORS

(71) Applicant: Robert Bosch GmbH, Stuttgart (DE)

(72) Inventor: Andreas Michalske, Kornwestheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 487 days.

(21) Appl. No.: 14/362,777

(22) PCT Filed: Oct. 17, 2012

(86) PCT No.: PCT/EP2012/070531
§ 371 (c)(1),
(2) Date: Jun. 4, 2014

(87) PCT Pub. No.: WO2013/087262
PCT Pub. Date: Jun. 20, 2013

(65) Prior Publication Data
US 2015/0039256 A1 Feb. 5, 2015

(30) Foreign Application Priority Data

Dec. 12, 2011 (DE) ........................ 10 2011 088 296

(51) Int. Cl.
*G01N 33/00* (2006.01)
*F02D 41/14* (2006.01)
(Continued)

(52) U.S. Cl.
CPC ........... *G01N 33/0006* (2013.01); *F01N 9/00* (2013.01); *F01N 11/00* (2013.01);
(Continued)

(58) Field of Classification Search
CPC .................................................. G01N 33/0006
See application file for complete search history.

(56) References Cited

U.S. PATENT DOCUMENTS 6,382,198 B1 * 5/2002 Smith ................. F02D 41/0085
123/673
8,245,566 B2 8/2012 Wehmeier et al.
(Continued)

FOREIGN PATENT DOCUMENTS

CN 102102593 A 6/2011
DE 10 2009 028 367 2/2001
(Continued)

OTHER PUBLICATIONS

International Search Report for PCT/EP2012/070531, dated Apr. 15, 2013.

*Primary Examiner* — Manuel L Barbee
*Assistant Examiner* — Raymond Nimox
(74) *Attorney, Agent, or Firm* — Norton Rose Fulbright US LLP; Gerard Messina

(57) ABSTRACT

In a method for dynamic monitoring of gas sensors of an internal combustion engine, in the event of a change of the gas state variable to be measured, a dynamic diagnosis is carried out based on a comparison of a measured signal which is an actual value of an output signal of the gas sensor and a modeled signal which is a model value. The output signal of the gas sensor is filtered using a high-pass filter and higher-frequency signal components are analyzed.

17 Claims, 3 Drawing Sheets

(51) Int. Cl.
*F01N 9/00* (2006.01)
*F01N 11/00* (2006.01)
*G01M 15/10* (2006.01)
*F02D 41/22* (2006.01)

(52) U.S. Cl.
CPC ..... *F02D 41/1454* (2013.01); *F02D 41/1458* (2013.01); *F02D 41/1495* (2013.01); *G01M 15/10* (2013.01); *F01N 2900/0404* (2013.01); *F01N 2900/0414* (2013.01); *F01N 2900/0416* (2013.01); *F02D 41/222* (2013.01); *F02D 2041/1432* (2013.01); *F02D 2041/1433* (2013.01)

(56) References Cited

U.S. PATENT DOCUMENTS

| | | | | |
|---|---|---|---|---|
| 2009/0248280 A1* | 10/2009 | Korbel | ................ | F02D 41/1454 701/109 |
| 2009/0254264 A1* | 10/2009 | Kirstaetter | .......... | F02D 41/1454 701/109 |
| 2009/0260429 A1* | 10/2009 | Wehmeier | ............. | F01N 11/007 73/114.73 |
| 2010/0083743 A1* | 4/2010 | Wehmeier | ........... | F02D 41/1495 73/114.72 |
| 2010/0089033 A1* | 4/2010 | Rosel | ................. | B01D 53/9409 60/276 |
| 2011/0082622 A1* | 4/2011 | Wehmeier | ............ | F01N 11/007 701/29.2 |
| 2011/0184700 A1 | 7/2011 | Muchalske et al. | | |
| 2012/0222474 A1* | 9/2012 | Plonka | ................ | F02D 41/1454 73/114.69 |

FOREIGN PATENT DOCUMENTS

| | | |
|---|---|---|
| DE | 10 2008 001 121 | 10/2009 |
| DE | 10 2008 001 569 | 10/2009 |
| DE | 10 2008 040 737 | 1/2010 |
| DE | 10 2008 042 549 | 4/2010 |
| EP | 1 074 718 | 2/2001 |
| EP | 2 336 532 | 6/2011 |
| JP | H02221647 A | 9/1990 |
| JP | 05263626 A | 10/1993 |
| JP | 2006511755 A | 4/2006 |
| JP | 2009074556 A | 4/2009 |
| JP | 2009250238 A | 10/2009 |
| JP | 2010096015 A | 4/2010 |

* cited by examiner

METHOD AND DEVICE FOR DYNAMIC MONITORING OF GAS SENSORS

BACKGROUND OF THE INVENTION

1. Field of the Invention

The present invention relates to a method and a device for dynamic monitoring of gas sensors of an internal combustion engine, e.g., as exhaust gas sensors or as gas concentration sensors in a supply air channel, the gas sensors having a low-pass behavior, and in the event of a change of the gas state variable to be detected on the basis of a comparison of a modeled signal and a measured signal, a dynamic diagnosis being carried out.

2. Description of the Related Art

To reduce the emissions in passenger automobiles having gasoline engines, 3-way catalytic converters are generally used as emission control systems, which only convert a sufficient amount of exhaust gases if air-fuel ratio $\lambda$ is regulated with high precision. For this purpose, air-fuel ratio $\lambda$ is measured with the aid of an exhaust gas sensor situated upstream from the emission control system. The storage capacity of such an emission control system for oxygen is used for the purpose of absorbing oxygen in lean phases and discharging it again in rich phases. In this way, oxidizable harmful gas components of the exhaust gas may be may be converted. An exhaust gas sensor connected downstream from the emission control system is used for monitoring the oxygen storage capacity of the emission control system. The oxygen storage capacity must be monitored within the scope of the on-board diagnosis (OBD), since it represents a measure of the conversion ability of the emission control system. To determine the oxygen storage capacity, either the emission control system is initially supplied with oxygen in a lean phase and subsequently emptied in a rich phase having a lambda value known in the exhaust gas under consideration of the passing exhaust gas quantity, or the emission control system is initially emptied of oxygen in a rich phase and subsequently filled up in a lean phase having a lambda value known in the exhaust gas under consideration of the passing exhaust gas quantity. The lean phase is ended when the exhaust gas sensor connected downstream from the emission control system detects the oxygen which may no longer be stored by the emission control system. A rich phase is also ended when the exhaust gas sensor detects the passage of rich exhaust gas. The oxygen storage capacity of the emission control system corresponds to the quantity of reducing agent supplied during the rich phase for emptying or the quantity of oxygen supplied during the lean phase for filling. The precise quantities are calculated from the signal of the upstream exhaust gas sensor and the exhaust gas flow rate ascertained from other sensor signals.

If the dynamic of the upstream exhaust gas sensor decreases, for example, as a result of soiling or aging, the air-fuel ratio may no longer be regulated with the required precision, so that the conversion performance of the emission control system decreases. Furthermore, deviations in the diagnosis of the emission control system may result, which may have the result that an emission control system which is operating correctly per se is incorrectly evaluated as nonfunctional. Lawmakers require a diagnosis of the sensor properties during driving operation, to ensure that the required air-fuel ratio may still be set sufficiently precisely, the emissions do not exceed the permissible limiting values, and the emission control system is correctly monitored. The OBD-II standards require lambda sensors and other exhaust gas sensors to be monitored not only with respect to their electrical operational reliability, but rather also with respect to their response behavior, i.e., worsening of the sensor dynamic must be recognized, which may be made noticeable by an increased time constant and/or reaction time. Reaction times and delay times between a change of the exhaust gas composition and its recognition must be checked on-board as to whether they are still permissible for the user functions, i.e., for control, regulating, and monitoring functions, which use the sensor signal. The reaction time from a mixture change up to the signal edge and a specific rise time, for example, from 0% to 63% or from 30% to 60% of a signal deviation, are generally used as characteristic variables for the dynamic properties of exhaust gas sensors. The reaction time also includes the gas runtime from the engine outlet up to the sensor and accordingly changes in particular in the event of a manipulation of the sensor installation site.

In diesel engines, broadband lambda sensors and, in conjunction with SCR catalytic converters, also $NO_x$ sensors are used as gas sensors or gas concentration sensors. $NO_x$ sensors additionally also deliver an $O_2$ signal. The $O_2$ signal of the broadband lambda sensor or $NO_x$ sensor is used in the diesel engine not only for the operation of exhaust aftertreatment units, but rather also for the internal-engine emission reduction. The measured $O_2$ concentration in the exhaust gas or the measured lambda signal is used to dynamically set the air-fuel mixture and thus minimize the scattering of the untreated emissions. In diesel engines having $NO_x$ storage catalytic converters (NSC), one broadband lambda sensor is required in each case upstream and downstream from the catalytic converter for a reliable description of the rich operation for regeneration. Internal-engine emission reduction and NSC operation also place specific minimum requirements on the dynamic properties of the $O_2$ sensor. The rise time of the $O_2$ signal is presently monitored during the transition from load to coasting, i.e., during the rise from a specific percentage below the normal $O_2$ content of air to 21%. If the sensor signal does not once reach a specific intermediate value after a maximum time, this is interpreted as a reaction time error. In diesel engines having $NO_x$ storage catalytic converters (NSC), the response behavior of the lambda sensors upstream and downstream from the catalytic converter is generally also compared.

For upcoming vehicle generations or model years, it is to be expected that monitoring of the sensor dynamic upon falling $O_2$ concentrations will also be required. In addition, in hybrid vehicles, there will no longer be coasting phases and therefore no phases having a constant $O_2$ concentration of 21%. First approaches for these additional requirements are the active monitoring in published German patent application document DE 10 2008 001 121 A1 and the observer-based method in published German patent application document DE 10 2008 040 737 A1.

A method for monitoring dynamic properties of a broadband lambda sensor is known from published German patent application document DE 10 2008 040 737 A1, a measured lambda signal being determined with the aid of the broadband lambda sensor, which corresponds to an oxygen concentration in the exhaust gas of an internal combustion engine, an observer being assigned to the internal combustion engine, which generates a modeled lambda signal from input variables, and an estimated error signal being formed, as an input variable of a controller connected upstream in the observer from a model, from the difference of the modeled lambda signal and the measured lambda signal or from the difference of a signal derived from the modeled lambda signal and a signal derived from the measured lambda signal. It is provided that a measure of the dynamic properties of the broadband lambda sensor, which are characterized by a response time and a reaction time, is determined from an evaluation of the estimated error signal or a variable derived therefrom, and the measure for the dynamic properties is compared to predefined limiting values to evaluate to what extent the dynamic properties of the broadband lambda sensor are sufficient for a provided operation of the internal combustion engine.

In addition, a method and a device for online adaptation of an LSU dynamic model are described in published German patent application document DE 10 2008 001 569 A1. The publication specifically relates to a method and a device for adapting a dynamic model of an exhaust gas sensor, which is a component of an exhaust duct of an internal combustion engine and using which a lambda value for regulating an air-fuel composition is determined, a simulated lambda value being calculated in a control unit or in a diagnostic unit of the internal combustion engine in parallel thereto and both the simulated lambda value and the measured lambda value being used by an application function. It is provided that during ongoing vehicle operation, a jump behavior of the exhaust gas sensor is determined by analyzing a signal change upon excitation of the system and the dynamic model of the exhaust gas sensor is adapted on the basis of these results.

For the identification of the sensor properties, known functions for dynamic monitoring of broadband lambda sensors are resorted to. For other gas concentration signals of exhaust gas sensors, for example, for an $NO_x$ signal, comparable requirements apply as for $O_2$ signals or $O_2$ sensors. Similarities between the monitoring functions are therefore to be assumed.

The method as recited in published German patent application document DE 10 2008 001 121 A1 is an active monitoring. It includes an excitation by a test injection, which increases both the fuel consumption and the emissions. The method according to published German patent application document DE 10 2008 040 737 A1 does operate passively, but presumes a so-called observer, the application of which is complex. In addition, both methods are primarily targeted to the recognition of greater reaction time changes.

BRIEF SUMMARY OF THE INVENTION

The object therefore exists of providing dynamic monitoring for gas sensors, which meets at least a part of the following requirements:
   particular suitability for the diagnosis or identification of rise times,
   uniform monitoring principle for increase and decrease of a gas concentration,
   passive method, i.e., without intervention into the air system or the fuel system of the internal combustion engine,
   applicable also in vehicles without coasting phases and without idle speed (for example, in hybrid vehicles),
   high availability in the relevant certification cycles,
   high robustness against disturbances, and
   low complexity and small application outlay.

It is furthermore an object of the present invention to provide a corresponding device for carrying out the method. The object relating to the method is achieved in that the output signal of the gas sensor is filtered using a high-pass filter, and in the event of a change of the gas state variable to be measured, also of a gas concentration, higher-frequency signal components are analyzed. A change may occur due to an excitation of the internal combustion engine.

Using this method, changes with respect to the dynamic response in gas sensors may be detected and quantified. Gas sensors within the meaning of the present invention are sensors which may measure the states of a gas or may detect changes. The state of the gas may be described by a temperature of the gas, a gas pressure, a gas flow rate, and/or a concentration of a specific gas component, for example, an oxygen content or $NO_x$ content. Gas sensors have a typical low-pass behavior, which is dependent, inter alia, on the geometry of their configuration. In addition, such sensors may change their response behavior as a result of aging or other influences (for example, as a result of sooting in diesel engines). In the time domain, the decreasing limiting frequency is expressed in a longer rise time, i.e., in the event of unchanged excitation, the signal edges become flatter. Therefore, if one connects a suitable high-pass filter, for example, a first-order high-pass filter in series with the sensor, in the event of steep changes of the gas state variable to be measured, for example, the gas concentration, on the output signal of the high-pass filter, one may recognize whether the limiting frequency of the low-pass filter is greater or less than the limiting frequency of the high-pass filter. If the sensor reacts sluggishly as a result of aging or external influences, only little or no higher-frequency signal components are determined in the event of changes of the gas state variables. If the sensor has a high level of dynamics, this has an effect on a relatively large high-frequency signal component, so that a dynamic diagnosis may be implemented using this feature. Using the provided method, a uniform monitoring principle may be provided for increasing and decreasing a gas state variable, for example, a gas concentration, which is designed passively, i.e., manages without an intervention into the air system or the fuel system of the internal combustion engine, as is the case in previous dynamic diagnostic methods. On the one hand, it has a high level of robustness against disturbances. On the other hand, the method is distinguished by its low complexity and by a small application outlay. The requirements mentioned at the outset in the statement of the object may therefore be met simultaneously.

In one preferred method variant, in the event of a change of an air-fuel ratio of an air-fuel mixture supplied to the internal combustion engine, the dynamic diagnosis of the gas sensor is carried out. The higher-frequency signal components are analyzed.

In order that it be possible to differentiate between a slow sensor and an inadequate excitation, the change speed of the gas state variable to be measured must be judged, without using the signal of the sensor to be monitored itself. In one preferred method variant, it is therefore provided that the higher-frequency signal components of the gas sensor are compared to corresponding high-pass-filtered output signals from a model of the gas sensor and the dynamic of the gas sensor is deduced on the basis of the comparison. In the case of the $O_2$ signal of a broadband lambda sensor or an $NO_x$ sensor, the air mass and the fuel mass are supplied as input variables for this purpose to the model, which predicts the residual oxygen concentration in the exhaust gas. The model simulates the gas sensor having its typical low-pass behavior, generally combined with a reaction time. The operational reliability of the real sensor may then be deduced by a comparison of the two high-pass outputs. In case of another gas concentration, for example, of an $NO_x$ signal, it may be necessary to use an additional untreated emission model.

In one preferred method variant, it is provided that both the higher-frequency signal components of the gas sensor and those of the model are squared and integrated and therefore higher-frequency energy components are calculated, and subsequently these energy components are used in the ratio and the dynamic behavior of the gas sensor is deduced on the basis of the energy ratio thus calculated. The smaller the area under the squared output signal of the high-pass filter, the slower the sensor or the excitation. Alternatively to the signal energies, variables may also be formed and used in the ratio which are closely related to the signal energies. For example, instead of the signal energy, the root of the signal energy may also be used or the absolute value of the high-pass filter output signal may be integrated.

In order that multiplicative errors of the gas sensor and/or the model or its input signals do not corrupt the signal comparison, scaling of the particular energy components is preferably carried out. Additive errors of the gas sensor or the model or its input signals do not have an effect, because a high-pass filter suppresses the constant component of a signal.

In the case of the ascertainment of the signal energies, it may be provided that the integration of the higher-frequency signal components is carried out with the aid of an integration duration $\Delta t$, which is individual for both signals, the point in time for the start of the integration of the two signals being triggered both in the case of a rising signal edge of the output signal and in the case of a falling signal edge. If rising and falling signal edges of the sensor signal do not have to be monitored separately, the method according to the present invention may be simplified. It is then alternatively possible to start the integration in both paths at an arbitrary point in time and carry it out for duration $\Delta t$. One condition is only a sufficient excitation by changes of the gas state variable to be measured, for example, the gas concentration, which originate from changing engine operating points, for example. Time interval $\Delta t$ may thus include multiple falling and rising edges. For the scaling, the particular maximum and minimum during $\Delta t$ is to be detected at both high-pass filter inputs.

One preferred method variant provides that, proceeding from a specific stationary point, upon beginning of the signal edges, an applicable signal deviation is waited out before the integration is started. A short-term stationary operation before the monitoring ensures that the signal edges of sensor and model originate from the same excitation also in the event of reaction time differences. This is important in particular if the installation site of the exhaust gas sensor has been manipulated.

If the energy ratio is compared to an applicable threshold value, which represents the dynamic of a marginal sensor, the threshold value and a model time constant $T_M$ selected in the model for the sensor being interdependent, a dynamic diagnosis may be carried out very easily. If $T_M$ already corresponds to a marginal sensor dynamic, the matching threshold value is at 1, so that its application is omitted. If model time constant $T_M$ corresponds to a sufficiently fast gas sensor, in contrast, for example, a nominal sensor, the monitoring limit for the energy ratio is less than 1. For the case in which the energy ratio the threshold value, the sensor is to be considered to be properly functioning; in the case in which the energy ratio≤the threshold value, the sensor is to be considered to be faulty.

The characteristic variables for the dynamic of the sensor are generally dependent on the gas flow rate, the gas volume flow, or the gas speed. If the diagnosis is to have a high selectivity in a large engine operating range, it is advantageous for the various filter time constants and/or the threshold value to also be tracked as a function of one of the preceding state variables. If the model does not simulate a marginal sensor, but rather a sufficiently fast sensor, i.e., a nominal sensor, for example, this also applies to the monitoring threshold value.

Upon inadequate excitation, the case may occur in principle that numerator and/or denominator of the energy ratio assume a value close to or equal to zero. The division by zero may be intercepted in that a check for sufficient excitation is carried out upon change of the gas state variable to be measured, for example, in the event of load changes of the internal combustion engine, the edge steepness being compared in the model signal, depending on the sign of the signal change, to an applicable threshold value. Alternatively, the check for sufficient excitation may be carried out in that the edge steepness of the input variables of the model is evaluated.

As an expansion of the diagnostic method, it may additionally be provided that an iterative identification of a sensor time constant $T_S$ is carried out, model time constant $T_M$ being adapted in steps as a function of the energy ratio of the signal components or of a variable dependent thereon. For this purpose, model time constant $T_M$ is initialized using a starting value $T_{init}$ and corrected in steps after each integration as a function of the energy ratio. To accelerate or decelerate the convergence of the iteration method, the adaptation may be carried out as a function of a variable dependent thereon instead of as a function of the energy ratio.

In one alternative method variant, an identification of sensor time constant $T_S$ may be carried out with the aid of values stored in a characteristic map for time constant $T_S$ or ratio values $T_S/T_M$, the value pairs energy ratio and model time constant $T_M$ or the numerator and denominator of the particular calculated energy ratio being used as input variables. This method is advantageous in particular with regard to a low computing outlay and therefore also with respect to the time until an identification result is present.

The diagnostic method according to the present invention may be used particularly advantageously in gas sensors which are used as gas pressure sensors, gas temperature sensors, gas flow rate sensors, or gas concentration sensors as exhaust gas sensors in the exhaust duct of the internal combustion engine as part of an exhaust gas monitoring and reduction system or in a supply air channel of the internal combustion engine, for example, in the intake manifold, to detect gas state variables or concentrations. These emission-relevant gas sensors must be monitored with respect to their dynamics and general function due to the requirements mentioned at the outset. Thus, for example, the response behavior of a gas pressure sensor may be monitored and a reduction of the dynamic may be detected if, for example, the attachment of the gas pressure sensor to an intake manifold is clogged or buckled. Gas temperature sensors or gas flow rate sensors may be designed, for example, as hot-film air flow meters inside a supply air channel of the internal combustion engine and in which a dynamic loss is to be registered as a result of soiling. If a suitable model may be specified for the signals of such sensors, the method according to the present invention, as described above in its method variants, may advantageously be applied.

In particular exhaust gas sensors in the form of broadband lambda sensors (LSU sensors) or $NO_x$ sensors come into consideration as gas sensors, using which an oxygen content in a gas mixture may be determined. For an exhaust gas sensor designed as a broadband lambda sensor or continuous lambda sensor, the measured oxygen concentration is preferably compared to a modeled oxygen concentration according to the above-described method variants for the diagnosis. Alternatively, the reciprocal lambda value may be used for this comparison, since it is approximately proportional to the oxygen concentration. Electrical variables are also suitable, which are proportional to the oxygen concentration, i.e., a voltage or a current in the sensor or in the associated circuit. The model signal used for the comparison must then be converted accordingly. For a nitrogen oxide sensor, the output signal of the nitrogen oxide sensor is analyzed as the actual value, the model value being determined from a modeled $NO_x$ value. This diagnosis may therefore be applied particularly advantageously in gasoline engines or in lean mix engines, whose emission control system has a catalytic converter and/or units for nitrogen oxide reduction. In gas sensors which are installed downstream from an emission control system, the influence of the emission control on the gas concentration of interest must be considered in the model. Alternatively, it is conceivable to carry out the diagnosis only in phases in which the emission control has no influence on the gas concentration of interest.

A further application of the present invention with its above-described variants may be provided in general in processes having at least one sensor, in which the process may be approximated by a first-order filter having a time constant and optionally having a reaction time and the behavior of a slowed sensor may be described by an increased filter time constant. Fundamentally, the above-described advantages also result in this case with respect to a judgment of the response behavior of the sensor. In addition, such a process may be improved with respect to its regulating behavior, in that its controller is adapted to the changed time constant.

One preferred application of the method with its above-described variants provides the use in hybrid vehicles, for example, diesel hybrid vehicles, which do not have idle operating phases or coasting phases. It is particularly to be emphasized that the application in hybrid vehicles does not diminish the consumption reduction and $CO_2$ reduction potential, since test injections are not necessary and special engine operating states do not have to be requested.

A further preferred application of the method with its above-described variants provides the use in vehicles which have a so-called sailing operation. In such vehicles, coasting operation is also largely omitted. Instead of entraining the engine during coasting, during sailing operation the clutch is disengaged, the engine goes into idle speed, and the vehicle rolls as a result of its inertia. Substantial consumption reduction and $CO_2$ reduction potentials also result in this case.

The object relating to the device is achieved in that, to carry out the method according to the present invention, a diagnostic unit is provided, which has a high-pass filter for analyzing higher-frequency signal components in the event of a change of the gas state variable to be measured and at least one model for the sensor having a low-pass behavior and calculating units, for example, integration units, comparators, and optionally characteristic map units for carrying out the dynamic diagnosis according to the above-described method variants. The functionality of the diagnostic unit may be implemented at least partially in software-based form, this being able to be provided as a separate unit or as part of a higher-order engine controller.

The present invention will be explained in greater detail hereafter on the basis of an exemplary embodiment shown in the figures.

DETAILED DESCRIPTION OF THE INVENTION

Figure 1:
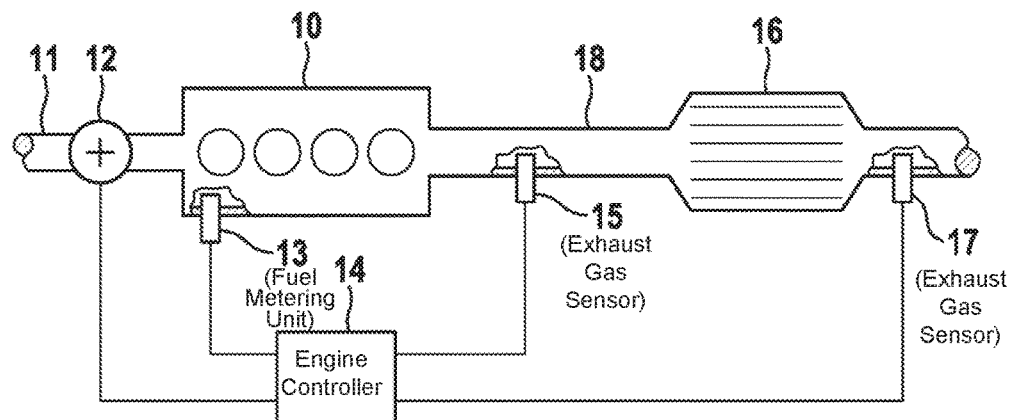
FIG. 1 shows a schematic view of the technical environment in which the method according to the present invention may be applied.

FIG. 1 schematically shows, in an example of a gasoline engine, the technical environment in which the method according to the present invention may be used for diagnosing an exhaust gas sensor 15. Air is supplied to an internal combustion engine 10 via an air supply 11 and its mass is determined using an air flow meter 12. Air flow meter 12 may be designed as a hot-film air flow meter. The exhaust gas of internal combustion engine 10 is discharged via an exhaust duct 18, an emission control system 16 being provided in the flow direction of the exhaust gas downstream from internal combustion engine 10. Emission control system 16 generally includes at least one catalytic converter.

To control internal combustion engine 10, an engine controller 14 is provided, which supplies fuel to internal combustion engine 10 via a fuel metering unit 13, on the one hand, and to which the signals of air flow meter 12 and exhaust gas sensor 15 situated in exhaust duct 18 and an exhaust gas sensor 17 situated in exhaust gas line 18 are supplied, on the other hand. In the example shown, exhaust gas sensor 15 determines a lambda actual value of a fuel-air mixture supplied to internal combustion engine 10. It may be designed as a broadband lambda sensor or as a continuous lambda sensor. Exhaust gas sensor 17 determines the exhaust gas composition downstream from emission control system 16. Exhaust gas sensor 17 may be designed as a bistable sensor or binary sensor.

With respect to improved dynamic monitoring of exhaust gas sensor 15, it is provided according to the present invention that high-pass and low-pass filters are used to check, in the event of a load change of internal combustion engine 10, whether the higher-frequency components of a concentration change are still recognized by exhaust gas sensor 15. Such gas sensors have a typical low-pass behavior, which is dependent, inter alia, on the geometry of their protective tube. In diesel engines, such a protective tube may additionally become sooted, whereby the bandwidth of the sensor decreases. In the time range, the decreasing limiting frequency is expressed in a greater rise time, i.e., the signal edges become flatter with unchanged excitation. Therefore, if a suitable high-pass filter is connected in series with the sensor, it may be recognized in the event of steep load changes on the output signal of the high-pass filter whether the limiting frequency of the low-pass filter is greater or less than the limiting frequency of the high-pass filter.

Figure 2A:
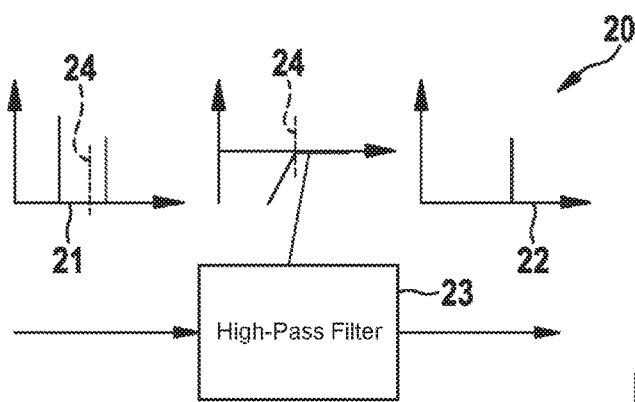
FIGS. 2a and 2b show Bode diagrams for a fast gas sensor and a slow gas sensor, respectively.
Figure 2B:
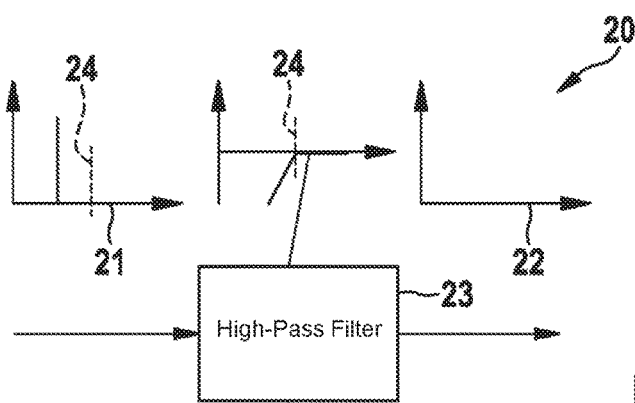

FIGS. 2a and 2b schematically show, on the basis of Bode diagrams 20, the functional principle. An input spectrum 21 developed in simplified form as a line spectrum including two frequency components and a first-order high-pass filter 23, the transfer function of which may be described by the equation $$G(j\omega)=T_F j\omega/(T_F j\omega+1) \quad (1)$$

where $T_F$ is the limiting frequency of the filter (filter limiting frequency 24). If the limiting frequency of exhaust gas sensor 15 exceeds limiting frequency $T_F$ of first-order high-pass filter 23, the series circuit behaves like a bandpass filter, i.e., the high frequencies of input spectrum 21 of exhaust gas sensor 15 are still transmitted and may be detected in output spectrum 22, as schematically shown in FIG. 2a. In contrast, if the limiting frequency of exhaust gas sensor 15 decreases, as a result of a dynamic loss, below limiting frequency $T_F$ of first-order high-pass filter 23 (filter limiting frequency 24), the series circuit blocks all frequencies, so that no frequency components of any type may be measured in output spectrum 22 (FIG. 2b). It is to be noted that this line spectrum is only used to explain the principle. The real frequency spectrum of an exhaust gas sensor 15 may be described by continuously extending frequency components.

In principle, the present invention is not restricted to first-order high-pass filters. Rather, any arbitrary other high-pass filters may also be used. The monitoring method is also applicable if the low-pass filter including exhaust gas sensor 15 is itself parameterized differently, for example, using a limiting frequency instead of the time constant, or has a higher order.

In order that a differentiation may be made between a slow exhaust gas sensor 15 and an inadequate excitation, the change speed of the exhaust gas composition must be judged, which may be carried out, for example, in the case of a broadband lambda sensor on the basis of air mass and fuel mass change. This may be carried out using a similar series circuit of filters. In the case of a broadband lambda sensor, for this purpose, only the above-mentioned masses must be converted into an $O_2$ concentration and delayed using a low-pass filter, which corresponds to a functional exhaust gas sensor. This low-pass filter is then to be connected in series to a high-pass filter, which has the same transmission function as the real sensor. By comparing the two high-pass filter outputs, the operational reliability of the real sensor may be deduced. In the case of a different gas component, it may be necessary to use an additional untreated emission model.

Figure 3:
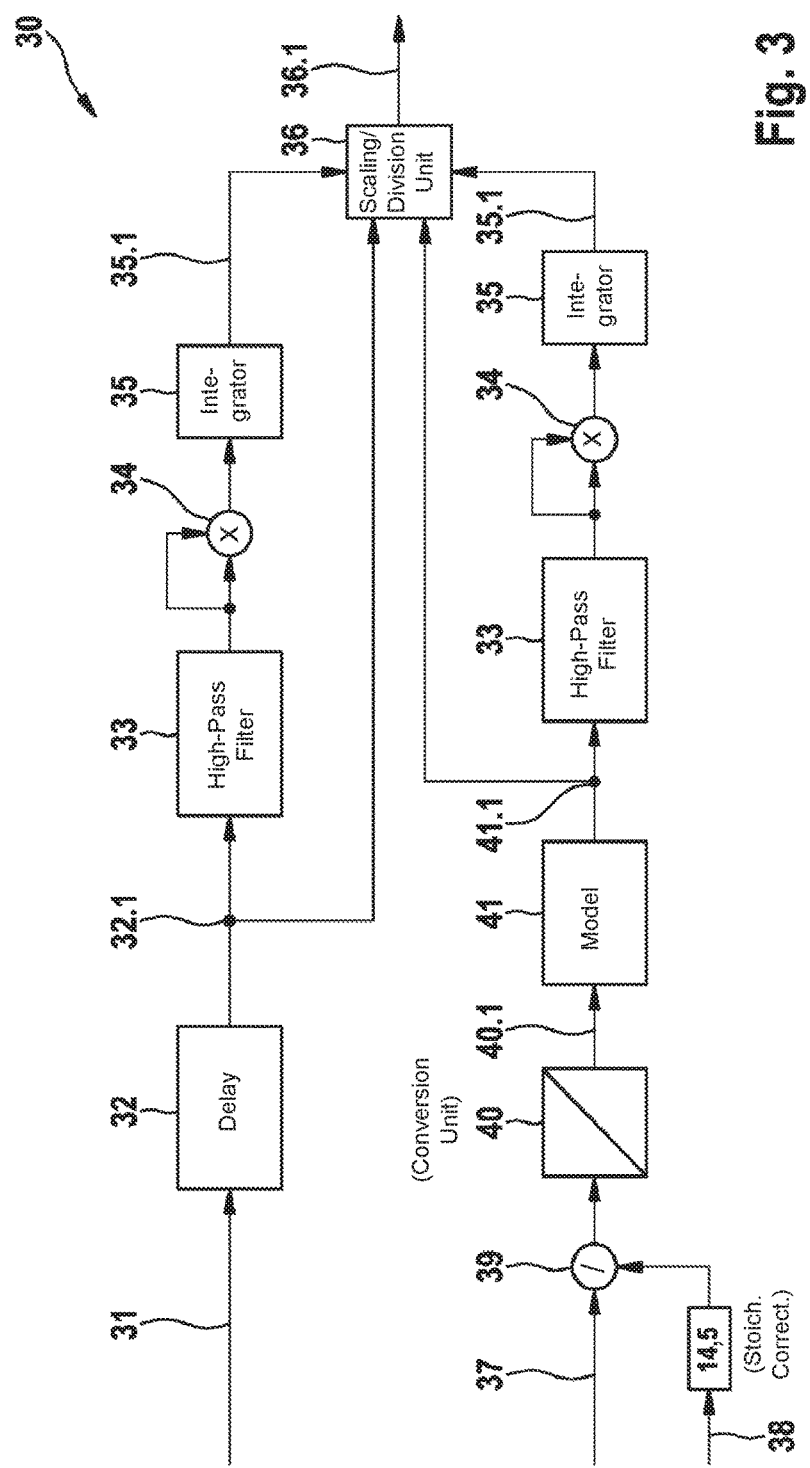
FIG. 3 shows a block diagram of a dynamic diagnostic circuit according to the present invention.

FIG. 3 shows a block diagram 30 of the functionality of the above-described principle in one preferred method variant. A path for an oxygen concentration 31 measured using exhaust gas sensor 15 is shown in the top part. As a result of a real gas run time and sensor delay 32, which may be described by a reaction time $T_I$ or a first-order low-pass filter having a sensor time constant $T_S$, an oxygen sensor signal 32.1 results from real oxygen concentration 31. The transmission function of sensor and gas run time 32 results from the following equation, $K_S$ representing an amplification factor for the sensor:

$$G(j\omega)=K_S \exp(-T_I j\omega/(T_S j\omega+1)) \quad (2)$$

$K_S$ generally corresponds to the multiplicative error or slope error of the sensor, which originates from production variation and aging. However, if the oxygen concentration is not used as the sensor signal, but rather a variable proportional thereto, $K_S$ is a corresponding transmission coefficient for converting the sensor signal into an oxygen concentration and may then also be dimension-afflicted. Subsequently, oxygen sensor signal 32.1 is filtered using a high-pass filter 33, whose transmission function corresponds to that of first-order high-pass filter 23 from FIG. 2a or 2b, and squared using a multiplier 34, which provides a signal which corresponds to a signal power. This signal is subsequently integrated with the aid of an integrator 35, so that a signal energy 35.1 of the higher-frequency energy components of the measured oxygen content is obtained. In a scaling and division unit 36 connected downstream, an energy ratio 36.1 E, which is a proportion measure for the higher-frequency energy components, results from a comparison to a correspondingly prepared signal for a value determined by model.

The preparation of the energy value determined by model is shown in the lower part of block diagram 30. A quotient is formed from an air mass 37 $m_L$ and a setpoint fuel mass 38 $m_K$ for fuel metering 13 after stoichiometric correction in a division unit 39 and a lambda value is calculated. Fuel mass 38 may result from the intended torque, which the driver specifies and which is converted into a fuel quantity. In a conversion unit 40, a calculated oxygen content 40.1 is determined from the lambda value. According to a model 41, using the transmission function $$G(j\omega)=K_S \exp(-T_{IM} j\omega/(T_M j\omega+1)) \quad (3)$$

a modeled oxygen content 41.1 is calculated, $T_{IM}$ representing a model reaction time and $T_M$ representing a model time constant. Subsequently, modeled oxygen content 41.1 is filtered using a further high-pass filter 33, whose transmission function corresponds to that of first-order high-pass filter 23 from FIG. 2a or 2b, and squared using a further multiplier 34, which provides a signal which corresponds to a signal power. This signal is subsequently integrated with the aid of a further integrator 35, so that a signal energy 35.1 for the higher-frequency energy components of the modeled oxygen content is obtained.

The integration of the squared signal delivers a measure of the energy of the higher-frequency components of particular $O_2$ signal 32.1, 41.1. The smaller the area under the squared output signal of high-pass filter 33, the slower the sensor or the excitation. Alternatively to the signal energies, variables may also be formed and set in a ratio, which are closely related to the signal energies. For example, instead of the signal energy, the root of the signal energy may also be used or the absolute value of the high-pass filter output signal may be integrated. The ratio of such replacement variables must be 1 if the energy ratio is 1, i.e., if the dynamic behavior of gas sensor and model is identical.

In order that multiplicative errors of the gas sensor and/or the model or its input signals do not corrupt the signal comparison, they are largely eliminated by scaling as follows. Energy ratio 36.1 E may accordingly be represented as follows:

$$E = \frac{(Um(t1+\Delta t) - Um(t1))^2 \int_{t0}^{t0+\Delta t}(Ys(t))^2 dt}{(Us(t0-\Delta t) - Us(t0))^2 \int_{t1}^{t1+\Delta t}(Ym(t))^2 dt} \quad (4)$$

therein, $U_S$ and $Y_S$ represent the high-pass input and output, respectively, in the signal path of the sensor and $U_M$ and $Y_M$ represent their counterparts in the model path. This means that $U_S$ corresponds to oxygen sensor signal 32.1 and $U_M$ corresponds to calculated oxygen content 40.1 from the model. The influence of the signal deviation of the excitation is also eliminated by the ratio formation.

The integration in the two signal paths does not necessarily have to be started simultaneously, but rather may be started in such a way that different reaction times do not influence the diagnosis result.

Figure 4:
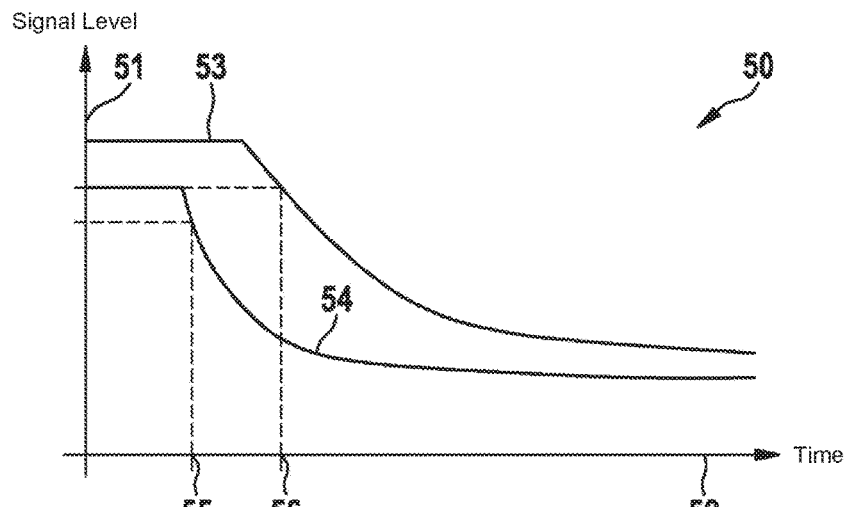
FIG. 4 shows a curve diagram for different signal paths.

FIG. 4 shows, in a curve diagram 50, points in time 55, 56 $t_1$, $t_0$ as examples for the start of the integration in the event of a falling edge. The signal level is shown as a function of time 52 for a signal curve sensor 53 and for a signal curve model 54. Proceeding from a specific stationary point, in the event of the beginning of a signal edge, a certain signal deviation is first covered before the integration is started. The individual integration duration may be of different lengths for the two paths. Furthermore, it may be provided that in the event of a rising signal edge, the integration is started, the procedure then continuing accordingly. A short-term stationary operation prior to the monitoring ensures that the signal edges of sensor and model also originate from the same excitation in the event of reaction time differences. This is important in particular if the installation site of exhaust gas sensor 15 was manipulated.

If rising and falling edges of the sensor signal do not have to be monitored separately, i.e., if so-called pinpointing is not necessary, the method according to the present invention may be simplified per se. It is alternatively possible to start the integration in both paths at an arbitrary point in time $t_0$ and to carry it out for duration $\Delta t$. The only condition is a sufficient excitation by change of the gas concentration or state variable to be measured, for example, as a result of changing engine operating points. Time interval $\Delta t$ may thus include multiple falling and rising edges. The particular maximum and minimum during $\Delta t$ is to be detected at both high-pass inputs for the scaling. Energy ratio 36.1 E for the diagnosis and/or identification then reads:

$$E = \frac{(Um, \max - Um, \min)^2 \int_{t0}^{t0+\Delta t} (Ys(t))^2 dt}{(Us, \max - Us, \min)^2 \int_{t0}^{t0+\Delta t} (Ym(t))^2 dt} \quad (5)$$

where $U_{s/m}=O_2$ concentration measured using the sensor/determined from the model $Y_{s/m}$=high-pass filter output signal sensor/model $U_{s/m,max}$=maximum of the high-pass filter input signal in interval $\Delta t$ $U_{s/m,min}$=minimum of the high-pass filter input signal in interval $\Delta t$ $\Delta t \gg T_{IM}$, $T_t$, i.e., integration duration>>model reaction time $T_{IM}$ or sensor reaction time $T_t$ A dynamic error of exhaust gas sensor 15 may be deduced from the value of energy ratio 36.1 E as follows: If the above-mentioned division of signal energies 35.1 results in a value greater than one, the real sensor is faster than the model. If the fraction is less than one, the real sensor is slower than the model.

Above-mentioned energy ratio 36.1 E is compared to a threshold value, which represents the dynamic of a marginal sensor. This threshold value is dependent on how model time constant $T_M$ was selected. If $T_M$ already corresponds to a marginal sensor dynamic, the matching threshold value is at 1, so that its application is omitted. If model time constant $T_M$ corresponds to a sufficiently fast gas sensor, in contrast, for example, a nominal sensor, the matching threshold value is less than 1. For the case in which energy ratio 36.1 E≥the threshold value, exhaust gas sensor 15 is to be considered to be properly functioning; in the case in which energy ratio 36.1 E≤the threshold value, exhaust gas sensor 15 is to be considered to be faulty.

In the event of a lacking excitation, the case may occur in principle that numerator and/or denominator of E in equation (4) will go to zero. The division by zero may be intercepted in that a test for sufficient excitation is carried out. For this purpose, for example, the model path may optionally additionally be implemented for a nominal sensor and it may be checked whether calculated oxygen content 40.1 or model oxygen content 41.1 has a sufficient edge steepness. In one preferred variant of this test, it is established whether the associated high-pass filter output, in the event of positive edges for calculated oxygen content 40.1 or for modeled oxygen content 41.1, exceeds a specific positive threshold value or, in the event of negative edges, falls below a specific negative value.

Figure 5:
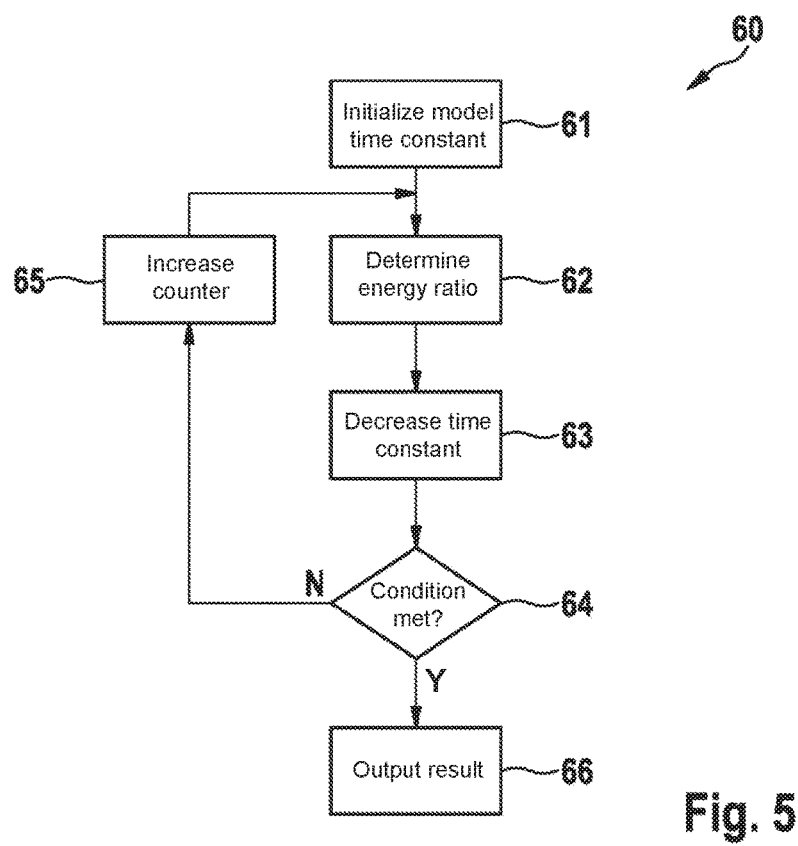
FIG. 5 shows a flow chart for an iterative identification of a sensor time constant TS.

The present invention may be expanded, so that an iterative identification of sensor time constant $T_S$ is also possible therewith. FIG. 5 shows the functional sequence in a flow chart 60.

For this purpose, in an initialization unit 61, model time constant $T_M$ is initialized using a starting value $T_{init}$ and then corrected after each integration as a function of energy ratio 36.1 E. For this purpose, a value $E_k$ is determined in function unit 62 by measuring and analysis. The following equation applies:

$$k=1, T_{M,k}=T_{init} \quad (6)$$

If $T_M$ is greater than sought value $T_S$, the sensor is faster than the model and energy ratio 36.1 E is greater than one. In this case, $T_M$ is decreased in the next step, in that it is divided by E, which is carried out in calculation unit 63. In the case in which $T_M<T_S$ is E<1 and the following division $T_M/E$ raises new model time constant $T_{M,k+1}$, the iteration rule therefore reads:

$$T_{M,1}=T_{init} \quad (7a)$$

$$T_{M,k+1}=T_{M,k}/E_k \quad (7b)$$

Where k denotes the kth iteration step. In the course of the integration, $E_k$ converges toward 1 and $T_{M,k}$ converges toward $T_S$. It is unimportant whether $T_{M,k}$ moves strictly monotonously toward $T_S$ or oscillates around $T_S$ with decreasing amplitude. This applies correspondingly for $E_k$. The iteration is ended when $$1-\varepsilon < E_k < 1+\varepsilon \text{ or } |E_k-1| < \varepsilon \quad (8).$$

This check is performed with the aid of query 64. If the above-mentioned condition is met, iteration $T_S=T_{M, k+1}$ is output as result 66. If the condition is not yet met, a counter 65 for k is increased by one.

The iterative identification may be carried out online, another excitation occurring in each iteration step. The iteration may also be carried out off-line, the same measurement being analyzed multiple times. If the present invention is used for the identification in this way, for the sensor diagnosis, the final value of $T_{M,k}$ must be compared to a marginal time constant. A comparison of E to 1 is then obviously no longer reasonable.

The convergence of the identification method may be accelerated or also slowed in that $E_k$ itself is not used for the calculation of $T_{M,k+1}$, but rather a variable dependent thereon. The iterative identification method searches for the solution $T_M=T_S$ of the equation E $(T_M)=1$. Alternatively, other numeric methods for solving so-called fixed point equations may be used for the iterative identification.

Alternatively, as a simple approach for a sensor identification, a characteristic map for estimated time constant $T_S$ may also be spanned. The following combinations of variables come into consideration as inputs for this characteristic map: $T_M$ and E or numerator and denominator of E (cf. (4) and (5)). $T_S$ or the ratio $T_S/T_M$ may be stored in the characteristic map.

The invention claimed is:

1. A method for dynamic monitoring of at least one gas sensor of an internal combustion engine to determine a fault status of the gas sensor during operation of the internal combustion engine, the gas sensor having a low-pass behavior depending on one of geometry, measuring principle, aging, or soiling, the method comprising:
measuring, using the gas sensor during the operation of the internal combustion engine in response to an operator torque request, a change of a gas state variable to produce a measured signal, which represents an actual value of the selected gas state variable output by the gas sensor;
checking for a sufficient excitation of the measured signal representing the gas state variable by comparing a steepness of a transition of a signal of an excitation model, the signal of the excitation model based on the operator torque request, to a predetermined threshold value;
upon detection of the sufficient excitation, performing a dynamic diagnosis of the gas sensor during the operation of the internal combustion engine, wherein the performing the dynamic diagnosis includes:
modeling operation of the gas sensor to produce a modeled signal;
placing a high-pass filter in series with the gas sensor, the high-pass filter having a limit frequency lower than a predetermined limit frequency of the low pass behavior of the gas sensor when the gas sensor is properly functioning, to filter the measured signal and the modeled signal modeling the gas sensor to produce higher-frequency components of the measured signal and higher-frequency components of the modeled signal;
squaring, using a multiplier, and integrating, using an integrator, the higher-frequency components of the measured signal and higher-frequency components of the modeled signal to produce higher-frequency signal energy components of the measured signal and higher-frequency signal energy components of the modeled signal;
comparing the higher-frequency signal energy components of the measured signal to the higher frequency signal energy components of the modeled signal;
determining a time constant of the sensor based on the comparing; and
determining the fault status of the gas sensor as indicating a faulty state of the gas sensor based on the comparing indicating that a low-pass limit frequency of the low-pass behavior of the gas sensor has decreased below the limit frequency of the high-pass filter as a result of aging of the sensor; and
regulating operation of the internal combustion engine as a function of the determined time constant.

2. The method as recited in claim 1, wherein the dynamic diagnosis of the gas sensor is performed in the event of a change of an air-fuel ratio of an air-fuel mixture supplied to the internal combustion engine.

3. The method as recited in claim 1, wherein the dynamic behavior of the gas sensor is deduced on the basis of an energy ratio of the calculated higher-frequency energy components.

4. The method as recited in claim 3, wherein the calculated higher-frequency energy components are scaled using a scaling unit.

5. The method as recited in claim 3, wherein the integration of the higher-frequency signal components of the gas sensor and the integration of the higher-frequency signal components of the modeled signal are each carried out with the aid of an individual integration duration, and wherein the start of the integration being triggered in the event of a rising signal edge of the measured signal and in the event of a falling signal edge.

6. The method as recited in claim 5, wherein, the start of the integration begins after an occurrence of a specified signal deviation starting from a specific stationary point.

7. The method as recited in claim 3, wherein the energy ratio is compared to a specified threshold value which represents the dynamics of a marginal sensor, and wherein the threshold value and a model time constant selected in a model for the sensor are interdependent.

8. The method as recited in claim 7, wherein at least one of filter time constants and the threshold value is tracked.

9. The method as recited in claim 7, wherein an iterative identification of the time constant of the sensor is carried out, the model time constant being adapted in steps as a function of the energy ratio.

10. The method as recited in claim 9, wherein an identification of the time constant of the sensor is carried out with the aid of values stored in a characteristic map.

11. The method as recited in claim 9, wherein the gas sensor is one of a gas pressure sensor, a gas temperature sensor, a gas flow rate sensor, or a gas concentration sensor.

12. The method as recited in claim 9, wherein the gas sensor is an exhaust gas sensor in the form of one of a broadband lambda sensor or a $NO_x$ sensor, using which an oxygen content in a gas mixture is determined.

13. A device for dynamic monitoring of at least one gas sensor in one of an exhaust duct of an internal combustion engine or an air supply channel of the internal combustion engine to determine a fault status of the gas sensor during operation of the internal combustion engine, the gas sensor having a low-pass behavior depending on one of geometry, measuring principle, aging, or soiling, the device comprising:
a detection unit for measuring, using the gas sensor during the operation of the internal combustion engine in response to an operator torque request, a change of a gas state variable to produce a measured signal, which represents an actual value of the selected gas state variable output by the gas sensor; and
a diagnostic unit for performing a dynamic diagnosis during the operation of the internal combustion engine, wherein the diagnostic unit:
checks for a sufficient excitation of the measured signal representing the gas state variable by comparing a steepness of a transition of a signal of an excitation model, the signal of the excitation model based on the operator torque request to a predetermined threshold value;
upon detection of the sufficient excitation, places a high-pass filter in series with the gas sensor, the high-pass filter having a limit frequency lower than a predetermined limit frequency of the low pass behavior of the gas sensor when the gas sensor is properly functioning, to filter the measured signal and a modeled signal modeling the gas sensor to produce higher-frequency components of the measured signal and higher-frequency components of the modeled signal;

squares, using a multiplier, and integrates, using an integrator, the higher-frequency components of the measured signal and higher-frequency components of the modeled signal to produce higher-frequency signal energy components of the measured signal and higher-frequency signal energy components of the modeled signal;

compares the higher-frequency signal energy components of the measured signal to the higher frequency signal components of the modeled signal;

determines a time constant of the sensor based on the comparing; and determines the fault status of the gas sensor as indicating a faulty state of the gas sensor based on the comparing indicating that a low-pass limit frequency of the low-pass behavior of the gas sensor has decreased below the limit frequency of the high-pass filter as a result of aging or soiling of the sensor;

wherein the device regulates operation of the internal combustion engine as a function of the determined time constant.

14. A method for dynamic monitoring of at least one gas sensor of an internal combustion engine, the method comprising:

measuring, using the gas sensor during the operation of the internal combustion engine in response to an operator torque request, a change of a gas state variable to produce a measured signal, which represents an actual value of the selected gas state variable output by the gas sensor;

checking for a sufficient excitation of the measured signal representing the gas state variable by comparing a steepness of a transition of a signal of an excitation model, the signal of the excitation model based on the operator torque request, to a predetermined threshold value;

upon detection of the sufficient excitation, performing a dynamic diagnosis of the gas sensor during the operation of the internal combustion engine, wherein the performing the dynamic diagnosis includes:

modeling operation of the gas sensor to produce a modeled signal;

comparing higher-frequency signal energy components of the measured signal to higher frequency signal energy components of the modeled signal; and determining a time constant of the sensor based on the comparing; and regulating operation of the internal combustion engine as a function of the determined time constant.

15. The method of claim 14, wherein the performing the dynamic diagnosis further includes placing a high-pass filter in series with the gas sensor, the high-pass filter having a limit frequency lower than a predetermined limit frequency of a low pass behavior of the gas sensor when the gas sensor is properly functioning, to filter the measured signal and the modeled signal modeling the gas sensor to produce higher-frequency components of the measured signal and higher-frequency components of the modeled signal.

16. The method of claim 15, wherein the performing the dynamic diagnosis further includes squaring, using a multiplier, and integrating, using an integrator, the higher-frequency components of the measured signal and higher-frequency components of the modeled signal to produce higher-frequency signal energy components of the measured signal and higher-frequency signal energy components of the modeled signal.

17. The method of claim 15, wherein the performing the dynamic diagnosis further includes determining a fault status of the gas sensor as indicating a faulty state of the gas sensor based on the comparing indicating that a low-pass limit frequency of the low-pass behavior of the gas sensor has decreased below the limit frequency of the high-pass filter as a result of aging of the sensor.

* * * * *